United States Patent [19]

Hamacher et al.

[11] Patent Number: 4,612,010
[45] Date of Patent: Sep. 16, 1986

[54] INFILTRATION PUMP

[76] Inventors: Edward N. Hamacher, 725 S. Lincoln, Apt. C-4, Spokane, Wash. 99204; Mark A. Stolle, 21625 NE. 8th St., Redmond, Wash. 98053

[21] Appl. No.: 765,880

[22] Filed: Aug. 14, 1985

[51] Int. Cl.$^4$ .............................................. A61M 5/00
[52] U.S. Cl. ................................. 604/207; 604/218; 604/229; 222/340
[58] Field of Search ............. 604/187, 208, 218, 207, 604/135, 134, 212, 229; 222/340, 309, 336

[56] References Cited

U.S. PATENT DOCUMENTS

| | | |
|---|---|---|
| 928,351 | 7/1909 | Wilkinson . |
| 1,608,275 | 11/1926 | Grier et al. . |
| 3,290,946 | 12/1966 | Pursell .......................... 222/340 X |
| 3,669,111 | 6/1972 | Dubner ............................... 604/229 |
| 3,881,360 | 5/1975 | Jurado ................................ 222/309 |
| 3,905,521 | 9/1975 | Mead et al. ..................... 604/208 X |
| 4,063,662 | 12/1977 | Drummond et al. ............... 604/207 |
| 4,064,879 | 12/1977 | Leibinsohn ..................... 604/218 X |

FOREIGN PATENT DOCUMENTS

| | | |
|---|---|---|
| 31510 | 1/1908 | Fed. Rep. of Germany . |
| 372944 | 4/1923 | Fed. Rep. of Germany . |

Primary Examiner—John D. Yasko
Attorney, Agent, or Firm—Seed and Berry

[57] ABSTRACT

The infiltration pump has an outer cylinder and an inner piston mounted for reciprocal motion within the cylinder. A fluid displacing seal is attached to one end of the piston. A coil biasing spring is placed within the cylinder between the piston and the fluid dispensing end of the cylinder. One end of the spring is seated against the fluid dispensing end of the cylinder. The other end of the spring is seated against an adaptor section which transfers the biasing force of the spring evenly over the face of the fluid displacing seal.

18 Claims, 3 Drawing Figures

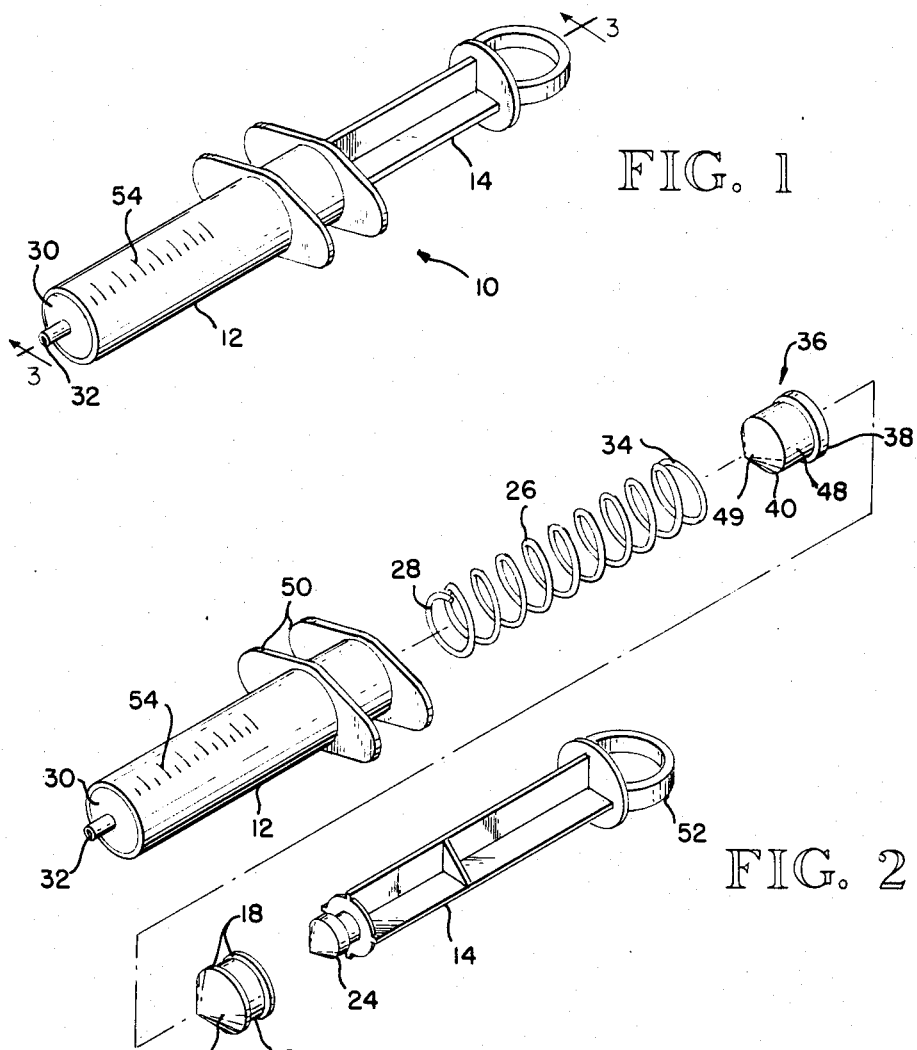
FIG. 1
FIG. 2
FIG. 3
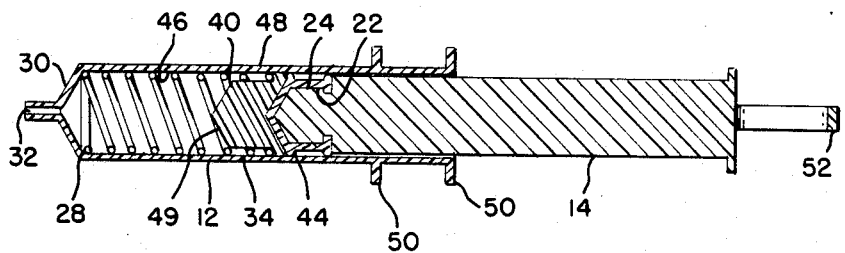

INFILTRATION PUMP

TECHNICAL FIELD

The invention relates to an improved hypodermic syringe. More specifically, the invention relates to an apparatus for biasing the piston of a hypodermic syringe to an extended position.

BACKGROUND OF THE ART

Modern surgery often requires the injection of large amounts of fluid into various parts of the body. Particularly, where reconstructive surgery is concerned, relatively large amounts of local anesthetics are injected into the subcutaneous tissues during surgery. These fluids often comprise local anesthetics which must infiltrate the entire area which is to be reconstructed.

Conventional hypodermic syringes having only a fluid containing cylinder and a fluid displacing piston are unsuitable for use in such surgery. Rather, syringes capable of pumping relative large amounts of such anesthetic on a substantially continuous basis must be used. Typically, such syringes employ biasing springs to return the fluid displacing piston to its original position after being depressed into the fluid displacing position. A check valve connecting the fluid cavity of the syringe with a fluid supply is included so that the physician can continually pump the handles of such a device to deliver a large quantity of fluid into the body.

Presently available syringes or pumps of the type described are bulky and virtually impossible to use in modern reconstructive surgery. Typically, these devices have springs which are external to the syringe cylinder to bias the piston to an extended position. Pump handles extend from the cylinder in a fashion similar to a conventional grease gun to depress the bias spring and fluid displacing piston. Thus, a serious disadvantage of the described device is that operation of the device in close proximity to the body is impaired by the projecting spring and handles. The construction of the device is necessarily complex and, therefore, costly. Devices of the type described are typically not disposable due to their expense. Therefore, a need exists for a disposable infiltration pump which provides minimum obstruction to close maneuvers about the body for the injection of subcutaneous tissue with suitable medications.

The described devices are also limited in that the biasing mechanisms cannot be adapted to conventional syringes for more conventional uses. For example, when a standard syringe is to be filled with a fluid prior to an injection, the user must puncture a vial constaining medication with the hypodermic needle and then draw the piston to fill the cylinder with medicine while holding the vial relative to the cylinder. Typically, the piston is then slightly depressed to bring fluid in the cylinder to the correct volume and to expel air. This procedure is wasteful, time consuming and inconvenient. It would be desirable to utilize the piston biasing technique of the previously described pump devices to draw fluid from the medicine vial in a controlled manner. However, the high cost, bulk and structural limitations of the described device precludes its use in this situation.

DISCLOSURE OF THE INVENTION

Therefore, it is an object of the present invention to provide an inexpensive, disposable infiltration pump for use in reconstructive surgery.

It is another object of the present invention to provide an infiltration pump which facilitates maneuvering the pump in close proximity to the body.

It is a further object of the present invention to provide an apparatus which is easily retrofittable to standard syringes to facilitate the loading of standard syringes with medicines.

The invention achieves these and other objects and advantages which will be apparent from the following disclosure by providing a standard syringe with an internal biasing spring and adaptor section to convert the syringe into a new and useful infiltration pump.

The infiltration pump has an outer cylinder and an inner piston mounted for reciprocal motion within the cylinder. A fluid displacing seal is attached to one end of the piston. A coil biasing spring is placed within the cylinder between the piston and the fluid dispensing end of the cylinder. One end of the spring is seated against the fluid dispensing end of the cylinder. The other end of the spring is seated against an adaptor section which transfers the biasing force of the spring evenly over the face of the fluid displacing seal.

The adaptor is constructed so as to cause the spring to evenly distribute its biasing force over the fluid seal without pinching any portion of the seal thus causing the seal to fail. The adaptor also maintains the axial alignment of the spring with the cylinder when the piston is depressed so that the biasing force remains evenly distributed over the seal throughout the travel of the piston. The coil spring has an external diameter selected so that the coil closely fits the internal diameter of the cylinder so that the inner wall of the cylinder prevents radial movement of the spring when the spring is reciprocated. The adaptor section also has an axially extending portion which fits inside the spring coil to trap the spring between the axially extending portion of the adaptor and the inside of the cylinder wall during reciprocal motion. Th combined effect of these features maintains a correct orientation of the spring within the cylinder during reciprocal motion so that the integrity of the seal is not defeated.

Appropriate means are provided on the outside of the cylinder and the free end of the piston so that the device can be operated with one hand.

The compressive force of the spring can be appropriately selected so that the spring only assists the user in retracting the piston or returns the piston to the extended position after the piston is fully depressed.

In use, the fluid dispensing end of the infiltration pump is joined to an infusion needle as disclosed in co-pending U.S. patent application Ser. No. 718,159, filed Apr. 1, 1985 by Edward N. Hamacher, for injecting subcutaneous tissue with local anesthetics or other medicines. A one-way valve is included at this junction to access a large fluid reservoir. Once the infusion needle has been inserted into the subcutaneous tissue or other area to be infiltrated, the piston is depressed into the cylinder to inject the fluid. Depending on the return force of the spring the piston will either return to its original position or will be spring-assisted to facilitate the return of the piston to the original position. The infiltration pump having been charged with a new volume of fluid through the one-way valve is then ready to inject this new volume of fluid into the patient. The infiltration pump described is no larger externally than a conventional syringe and therefore can be maneuvered very closely to the body during infiltration. This is especially advantageous during reconstructive surgery where the infusion needle is routed to various parts of the body during treatment through a single incision. It is imperative that the infiltration pump be maneuverable when held close to the body so that successful area infiltration can be achieved.

BRIEF DESCRIPTION OF DRAWING

FIG. 1 is an isometric view of the infiltration pump in accordance with the present invention;

FIG. 2 is an exploded isometric view of the infiltration pump showing the various internal parts; and FIG. 3 is a cross-sectional view taken along line 3—3 of FIG. 1.

BEST MODE FOR CARRYING OUT THE INVENTION

As shown in the figures, an infiltration pump, in accordance with the present invention is generally indicated at reference numeral 10. The infiltration pump has a fluid containing chamber, such as cylinder 12, and a reciprocating piston 14 with a fluid displacing seal 16. The seal 16 has circumferential radially extending ring seals 18 to prevent fluid from bypassing the seal as the piston is depressed into the cylinder. The ring seals 18 have a diameter slightly in excess of the internal diameter of the cylinder 12 so that the ring seals are slightly deformed when inserted in the cylinder. The fluid displacing seal 16 also has an axially facing fluid-displacing surface 20 at the forward end of the seal. The fluid seal is attached to the piston 14, such as by a socket and prong arrangement 22 and 24 as is conventionally understood.

The reciprocating piston 14 is biased to an extended position by a biasing coil spring 26. The spring has an external coil diameter selected so that the coil closely fits the internal diameter of the fluid-containing cylinder 12 so that the spring is restricted against radial movement when the piston is reciprocated. As best shown in FIG. 3, one end 28 of the biasing spring 26 seats against a fluid dispensing end 30 of the cylinder 12. The fluid dispensing end 30 has reduced diameter portion defining a fluid dispensing aperture 32.

The second end 34 of the coil biasing spring is seated against a spring adaptor generally indicated by reference numeral 36. The spring adaptor serves to distribute the biasing force of the spring evenly over the axially facing surface 20 of the seal 16. Thus, the spring adaptor prevents the spring from pinching or otherwise deforming the ring seals 18. In this way, the integrity of the seals is maintained regardless of the spring biasing force. The spring adaptor also serves to maintain the spring in axial alignment with the cylinder so that the spring does not force the adaptor itself out of axial alignment thus possibly violating the integrity of the seal.

The adaptor 36 accomplishes these functions according to the structural interaction of a mating-end portion 38 and spring-retaining portion 40. Both the mating-end portion 38 and the spring-retaining portion 40 are generally cylindrical in shape. The diameter of the mating-end portion 38 extends sufficiently to closely fit the interior diameter of the fluid-containing cylinder 12 to prevent substantial radial movement of the adaptor while allowing free axial movement thereof. As shown in FIG. 3, the mating-end portion 38 has a contact surface 44 which conforms to the shape of the axially facing surface 20 of the fluid-dispacing seal 16. Thus, the biasing force due to the spring 26 is evenly distributed over the axially facing surface 20 of the seal and is not transferred to the ring seals 18.

The diameter of the spring-retaining portion 40 is selected to closely fit the interior diameter of the coil biasing spring 26. The spring is, therefore, trapped between the inner wall 46 of the cylinder 12 and the outer surface 48 of the spring-retaining portion 40 as the piston reciprocates in the cylinder. In this way, the spring coils neatly around the adaptor when depressed and prevents the adaptor from becoming axially misaligned and exerting uneven forces on the fluid displacing seal 16. The forward end 49 of the adaptor is tapered to guide the spring onto the outer surface 48 of the spring retaining portion 40. The length of the spring-retaining portion 40 can be selected to approximate the compressed length of the spring 26 so that all the spring coils nest between the outer surface 48 of the spring-retaining portion and the inner wall 46 of the cylinder when the piston is fully depressed. This results in as much of the fluid in the syringe being forced out as possible when the piston is fully pressed into the cylinder.

The spring constant can be chosen so that the spring 26 overcomes frictional resistance between the piston and the cylinder 12, such as that caused by the ring seals 18, to return the piston 14 to its extended position after having been fully depressed into the cylinder. For example, for a cylinder having a length of approximately 70 mm and an internal diameter of approximately 22 mm a bias spring having a relaxed length of approximately 75 mm and a diameter of approximately 20 mm is preferably used. This preferred spring has a maximum compressive force of 10 to 15 ounces to return the piston to the extended position. Generally, the spring constant k varies inversely with the cross-sectional area of the cylinder if the cylinder dimensions are changed. Alternatively, the spring force can be selected to only assist the user in retracting the piston from the cylinder. That is, the maximum spring force being somewhat less than the frictional force between the piston and the cylinder.

The spring is preferrably constructed from a chemically inert material such as stainless steel. To improve the nonreactive character of the spring, a chemically inert coating, Teflon for example, can be applied thereto.

Flanges 50 are provided on the cylinder 12 to facilitate use of the infiltration pump 10 with one hand. The flanges are separated on the cylinder by a distance approximating a finger width so that forces in both axial directions can be applied to the cylinder. The piston is preferably provided with a thumb ring 52 or other means for applying axial forces to the piston 14. If a spring having a sufficient compressive force to return the piston to its extended position without assistance is selected, then the thumb ring 52 can be omitted.

The infiltration pump 10 as described is well adapted for use for infusion of medicines to various parts of the body. The pump as shown in FIG. 1 has no external protrusions to obstruct the use of the pump in close quarters. The exterior shape of the pump is no different from a conventional syringe and, therefore, usable wherever a conventional syringe may be. The pump is useful whenever a volume of fluid must be injected which exceeds the capacity of the fluid containing cylinder. Thus, the application of the invention is not limited to reconstructive surgery.

The fluid-containing cylinder 12 is provided with calibrations 54 which indicate the interior volume of the cylinder when the piston is in a variety of positions. The calibrations, must of course, account for the volume occupied by the coil biasing spring 26 and spring adaptor 36 as will be well understood by those skilled in the art. The length of the adaptor and spring when fully compressed are preferably selected to displace the piston by an increment of 10 volumetric units, or other convenient major volumetric increment, so as to permit easy use of the volumetric markings 54. This may involve comprising the length of the spring somewhat to achieve this desireable result.

The invention is also retrofitable and adaptable to conventional syringes to produce a syringe which can more easily and accurately meter the drawing of fluid into the cylinder. The spring 26 and adaptor section 36 can be manufactured in a variety of lengths and diameters to correspond to the interior diameter and length of various conventional syringes. As shown in FIGS. 2 and 3, the contact surface 44 of the spring adaptor 36 is preferably conical to adapt to the axially facing surface 20 of conventional syringe seals. Therefore, most syringes can be fitted with the spring 26 and adaptor 36 to return the piston to its extended position after depression. A physician when filling such a modified syringe from a vial would pierce the fluid retaining membrane of the vial with the hypodermic needle and then allow the biasing spring 26 to extend the piston thus filling the cylinder with fluid. Since the physician need not pull the piston out manually, while trying at the same time to hold the syringe and vial, filling of the syringe is facilitated enabling accurate charging of the cylinder with fluid.

When the spring 26 and spring adaptor 36 are provided as a retrofit kit the user will be informed of the volumetric adjustment which must be made for the calibrations on the resulting modified syringe.

When the infiltration pump shown in the figures is used for pumping a large volume of fluid, a check valve (not shown) and fluid supply (not shown) will typically be provided to charge the cylinder with a new volume of fluid upon each return of the piston to the extended position.

Additional embodiments and variations of the present invention utilizing the same inventive concepts herein described are contemplated. Therefore, the invention is not to be limited to the above description, but is to be determined in scope by the claims which follow.

We claim:
1. An infiltration pump for fluid, comprising:
an axially elongated body having an interior defining a hollow chamber of uniform internal cross-section for containing fluid and having an open end and an opposite fluid-dispensing end;
a fluid-displacing piston mounted for reciprocal motion within the chamber including a fluid displacing sea;
a biasing coil spring positioned inside the chamber between the fluid-dispensing end and the piston to bias the piston to an extended position, the spring sized to closely fit the inside of the chamber to prevent lateral movement of the spring; and
a spring adaptor inside the chamber and between the spring and piston having a first mating end portion for transferring the spring bias force evenly to the piston and second spring retaining portion to maintain the axial alignment of the spring with the chamber, the first mating end portion having a contact surface conforming to the end of the piston and a radially extending surface, extending laterally opposite the contact surface and to form a seat for one end of the spring, the second spring retaining portion extending axially from the first mating end portion and sized to closely fit the inside of the coil spring.

2. The infiltration pump of claim 1 wherein the second spring retaining portion extends axially away from the first mating portion a distance approximately equal to the compressed length of the biasing, coil spring to coil the spring neatly between the periphery of the second spring retaining portion and the chamber to maintain the spring and adaptor in substantial axial alignment with the cylinder and minimize retention of fluid in the pump when the piston is fully inserted.

3. The infiltration pump of claim 1 wherein the spring has maximum bias force when compressed which is sufficient to overcome the frictional forces between the piston and the chamber.

4. An infiltration pump for fluid, comprising:
an axially elongated hollow cylinder for containing fluid having an open end and a fluid-dispensing end and means on the outside of the cylinder near the open end for applying axial forces to the cylinder with the forefingers of one hand;
a fluid-displacing piston mounted for reciprocal motion within the cylinder, one end of the piston extending from the open end of the cylinder and having means for applying an axial force to the piston with the thumb of the hand in cooperation with the axial force applying means on the cylinder, the other end of the piston having a fluid displacing seal attached thereto having an axially facing fluid displacing surface and at least one circumferential, radially extending ring seal to contain fluid inside the cylinder;
a coil biasing spring inside the cylinder between the fluid-dispensing end and the piston to bias the piston to an extended position, a first end of the spring sized to seat against the fluid-dispensing end of the cylinder, the diameter of the spring sized to closely fit the inside of the cylinder to prevent substantial radial movement of the spring; and
a spring adaptor having a first mating end portion for transferring the spring bias force evenly over the axially facing fluid-displacing surface and a second spring retaining portion to maintain the axial alignment of the spring, the first mating end portion having a contact surface conforming to the fluid displacing seal axially facing surface and extending radially sufficiently to form a seat for the send end of the spring, the second spring retaining portion extending axially from the first mating end portion and having a diameter sized to closely fit the inside of the spring coil.

5. The infiltration pump of claim 4 wherein the second spring retaining portion extends axially away from the first mating portion a distance approximately equal to the compressed length of the coil biasing spring to coil the spring neatly between the periphery of the second spring retaining portion and the cylinder to maintain the spring and adaptor in substantial axial alignment with the cylinder.

6. The infiltration pump of claim 4 wherein the axial force applying means on the piston is capable of transferring a retracting force to the piston.

7. The infiltration pump of claim 6 wherein the spring has a maximum bias when compressed which is less than the frictional force between the piston and the cylinder.

8. The infiltration pump of claim 6 wherein the axial force applying means on the cylinder comprise first and second radially extending flanges, the first flange being closest to the open end of the cylinder for applying a compressive force to the piston, the second flange spaced approximately a finger width towards the fluid dispensing end of the cylinder for applying a retractive force to the piston.

9. The infiltration pump of claim 4 wherein the spring has a maximum bias force when compressed which is sufficient to overcome the frictional force between the piston and the cylinder.

10. The infiltration pump of claim 4 including calibrations on the cylinder to indicate the volume of fluid in the cylinder.

11. The infiltration pump of claim 4 wherein the bias spring is stainless steel.

12. The infiltratin pump of claim 4 wherein the bias spring is coated with a chemically inert material.

13. A spring bias adaptor kit for syringes of the type having a fluid containing cylinder with a reciprocating piston including a fluid-displacing seal on an end of the piston, comprising;

a biasing coil spring to bias the piston to an extended position having a diameter sized to closely fit the inside of the cylinder; and a spring adaptor having a first mating end portion having a contact surface adapted to fit against the fluid displacing seal and a second spring retaining portion extending axially from the first mating end portion to maintain spring in substantial axial alignment with the cylinder to reduce the amount of fluid retained in the syringe when the piston is fully inserted into the cylinder.

14. The adaptor kit of claim 13 wherein the first mating end portion includes a surface opposite the contact surface which extends radially to form a seat for one end of the spring and wherein the second spring retaining portion has a diameter sized to closely fit the inside of the spring.

15. The adaptor kit of claim 13 wherein the maximum bias force extended by the bias spring when compressed is sufficient to overcome the frictinal force between the piston and the cylinder.

16. The adaptor kit of claim 13 wherein the bias spring is stainless steel.

17. The adaptor kit of claim 13 wherein the bias spring is coated with a chemically inert material.

18. The adaptor kit of claim 13 wherein the length of the adaptor and spring are selected so that when the piston is fully inserted in the cylinder the piston is displaced longitudinally by a distance corresponding to a major volumetric increment.

* * * * *